US009724508B2

(12) United States Patent
Lamont et al.

(10) Patent No.: US 9,724,508 B2
(45) Date of Patent: Aug. 8, 2017

(54) ELECTRONIC IDENTIFICATION OF EXTERNAL CABLES FOR EXTERNAL MEDICAL DEVICES

(75) Inventors: Robert Lamont, Van Nuys, CA (US); Thomas Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 832 days.

(21) Appl. No.: 12/400,051

(22) Filed: Mar. 9, 2009

(65) Prior Publication Data

US 2010/0228324 A1 Sep. 9, 2010

(51) Int. Cl.
*A61N 1/00* (2006.01)
*A61N 1/08* (2006.01)
*A61N 1/05* (2006.01)
*A61N 1/04* (2006.01)
*A61N 1/375* (2006.01)
*A61N 1/372* (2006.01)
*A61N 1/36* (2006.01)

(52) U.S. Cl.
CPC ............ *A61N 1/08* (2013.01); *A61N 1/0551* (2013.01); *A61N 1/0476* (2013.01); *A61N 1/05* (2013.01); *A61N 1/056* (2013.01); *A61N 1/0534* (2013.01); *A61N 1/36071* (2013.01); *A61N 1/372* (2013.01); *A61N 1/3752* (2013.01); *A61N 2001/086* (2013.01); *A61N 2001/37294* (2013.01)

(58) Field of Classification Search
CPC ........ A61N 1/05; A61N 1/056; A61N 1/0551; A61N 1/0534; A61N 2001/086; A61N 1/0476; A61N 1/372; A61N 1/3752; A61N 2001/372; A61N 2001/37294; A61N 1/08; A61N 1/36071

USPC ..................................................... 607/116, 63
See application file for complete search history.

(56) References Cited

U.S. PATENT DOCUMENTS

| 5,400,267 A | * | 3/1995 | Denen .................... A61B 17/00 128/908 |
| 5,573,533 A | * | 11/1996 | Strul ............................... 606/34 |
| 6,381,496 B1 | * | 4/2002 | Meadows et al. .............. 607/59 |

(Continued)

OTHER PUBLICATIONS

Linke, Bernhard, Maxim Application Note 1796, "Overview of 1-Wire® Technology and its Use", http://pdfserv.maxim-ic.com/en/an/AN1796.pdf, Jun. 2008.

*Primary Examiner* — Lindsey G Wehrheim
(74) *Attorney, Agent, or Firm* — Lewis, Reese & Nesmith, PLLC

(57) ABSTRACT

Disclosed is an improved external cable box assembly and external trial stimulator (ETS) for use with an implantable medical device. The improved external cable box assembly has memory and logic circuitry embedded in it which allows the cable box to be identified. Associated logic circuitry in the improved ETS allows the ETS to read and write characteristics—such as electronic identifiers or cable addresses—of the external cable box assemblies and to store the values of those characteristics in its memory, associating characteristic values with each of its ports. If the external cable box assemblies become unplugged from the ETS and then are reconnected to incorrect ports on the ETS, logic in the ETS will either alert the patient to swap the port locations of the external stimulation cables, or the ETS will automatically reroute the correct therapy through each port.

36 Claims, 13 Drawing Sheets

(56) References Cited

U.S. PATENT DOCUMENTS

| | | | |
|---|---|---|---|
| 6,466,824 B1* | 10/2002 | Struble | 607/115 |
| 6,516,227 B1 | 2/2003 | Meadows et al. | 607/46 |
| 6,609,029 B1 | 8/2003 | Mann et al. | 607/37 |
| 6,741,892 B1 | 5/2004 | Meadows et al. | 607/116 |
| 7,239,916 B2* | 7/2007 | Thompson et al. | 607/30 |
| 2005/0273890 A1* | 12/2005 | Flaherty et al. | 901/50 |
| 2006/0030918 A1* | 2/2006 | Chinn et al. | 607/117 |
| 2008/0033510 A1* | 2/2008 | Herregraven et al. | 607/63 |
| 2009/0149917 A1* | 6/2009 | Whitehurst et al. | 607/59 |

* cited by examiner

ELECTRONIC IDENTIFICATION OF EXTERNAL CABLES FOR EXTERNAL MEDICAL DEVICES

FIELD OF THE INVENTION

The present invention relates to an improved apparatus, system and method for assuring the proper connection of external stimulation cables comprising part of an electronic medical device to an external trial stimulator.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227, which is hereby incorporated by reference in its entirety. However, the present invention may find applicability in many implantable medical device systems.

SCS is a well-accepted clinical method for reducing pain in certain populations of patients. As shown in FIGS. 1-2, an SCS system typically includes an Implantable Pulse Generator (IPG) 100, electrodes 106, at least one electrode lead (two such leads, 102a and 102b, are shown), and, optionally, at least one electrode lead extension 120. The electrodes 106, which reside on a distal end of the electrode leads 102a and 102b, are typically implanted along the dura 70 of the spinal cord, and the IPG 100 generates electrical pulses that are delivered through the electrodes 106 to nerve fibers within the spinal column 19. Individual electrodes 106 are arranged in a desired pattern and spacing to create an electrode array 110. Individual wires 112a-h within the electrode leads 102a and 102b connect with each electrode 106 in the array 110. The electrode leads 102a and 102b exit the spinal column and generally attach to one or more electrode lead extensions 120. The electrode lead extensions 120, in turn, are typically tunneled around the torso of the patient to a subcutaneous pocket where the IPG 100 is implanted. Alternatively, the electrode leads 102a and 102b may directly connect with the IPG 100.

In addition to precise placement of the electrode array in the dura 70, proper selection of the electrodes, i.e., which of the electrodes in the array should be active in a given patient, is critical for achieving effective stimulation therapy. However, because of the uncertainties of the distances of the electrodes from the neural target, the unknown nature of the specific conductive environment in which the electrode is placed, etc., the precise combination of active electrodes that will be perceived by a patient as providing optimal therapy generally cannot be known in advance. Moreover, the selected electrodes can be operated in many different modes (e.g., monopolar, bipolar, multipolar), and a given electrode can operate as a current source or sink with variable relative current amplitudes, pulse durations, and pulse frequencies. As a result, the patient may require that a different electrical stimulation therapy program be delivered through each lead, such that one stimulation therapy program is provided for the lead 102a implanted on the left side of the spinal column and a different stimulation therapy program is provided for the lead 102b implanted on the right side of the spinal column.

Determining these programs generally requires at the outset a "trial stimulation phase," in which various electrode and stimulation parameters are tried and feedback is received from the patient as to which of the combinations feels most effective. During the trial stimulation phase, the patient's response to a variety of stimulation parameters may be analyzed over a period of time prior to complete implantation of the electrical stimulation system into the patient. A trial stimulation phase may last for several days, or even one or more weeks. During the trial stimulation phase, a patient is typically able to make adjustments to received stimulation. For example, a patient may be able to turn the stimulation on and off, or adjust one or more stimulation parameters, such as stimulation amplitude, or switch between two or more different pre-programmed stimulation patterns, as desired.

As is shown in FIGS. 3 and 4, during the trial stimulation phase, the distal end of leads 102a and 102b are implanted into the patient at the selected location, while the proximal end of the leads are electrically coupled to an external trial stimulator (ETS) 140 via external cable box assemblies 142 (and, optionally, one or more trial stimulation cable extensions 132). Each external cable box assembly 142 consists of external cable box 150, trial stimulation cable 134, and male connector 135. As its name implies, the ETS 140 is external to (i.e., not implanted in) the patient. The ETS 140 generally mimics operation of the IPG 100, which at this point is not yet implanted, and allows different stimulation programs to be established for each lead 102a and 102b. Once these programs are determined, the IPG 100 may then be implanted, the determined programs written into the IPG 100, and the leads 102a and 102b coupled to the IPG for a completed implanted stimulation solution.

Because the trial stimulation phase may last up to several weeks, it is possible that the trial stimulation cables 134 (or their extensions 132) may become unplugged from the ETS 140. In the case of ETSs with multiple ports 141, if two or more external cable box assemblies 142a and 142b appear identical to the user, then the user may re-connect the trial stimulation cables 134a and 134b into different ports 141a and 141b on the ETS 140 than they were plugged into when the patient was designing the proper electrical stimulation therapy. This would result in, e.g., the stimulation therapy program designed for the right side of the patient's spinal column being delivered to the left side of the patient's spinal column and vice versa, thus potentially delivering undesired stimulation to the patient.

Presently, labels, implemented as stickers, are typically used to identify the proper connection of each external stimulation cable 134 to the appropriate port 141 on the ETS 140. However, these labels can become loose and fall off or can be confusing to some patients. Also, there is no failsafe in place in the system should the patient fail to or refuse to re-plug in the external stimulation cables 134 correctly.

Given these shortcomings, the art of implantable medical devices would benefit from an improved electronic, low-cost method for assuring the proper connection of external cables to an external trial stimulator, and this disclosure presents such a solution.

DETAILED DESCRIPTION

The description that follows relates to use of the invention within a spinal cord stimulation (SCS) system. However, it is to be understood that the invention is not so limited. Rather, the invention may be used with any type of implantable medical device that could benefit from an improved method of assuring the proper connection of external stimulation cables to an external trial stimulator.

Disclosed is an improved external cable box assembly and external trial stimulator (ETS) for use with an implantable medical device. Specifically, the improved external cable box assembly and ETS are used during a "test drive" or "trial stimulation phase" in which the patient and physician determine what type of electrical stimulation therapy will produce the most beneficial results to the patient before permanently implanting an IPG in the patient. The improved external cable box assembly has memory and logic circuitry embedded in it which allows the cable box to be identified. Associated logic circuitry in the improved ETS allows the ETS to read and write characteristics—such as electronic identifiers or cable addresses—of the external cable box assemblies and to store the values of those characteristics in its memory, associating characteristic values with each of its ports. If the external cable box assemblies become unplugged from the ETS and then are reconnected to incorrect ports on the ETS, logic in the ETS will either alert the patient to swap the port locations of the external stimulation cables, or the ETS will automatically reroute the correct therapy through each port.

Figure 1:
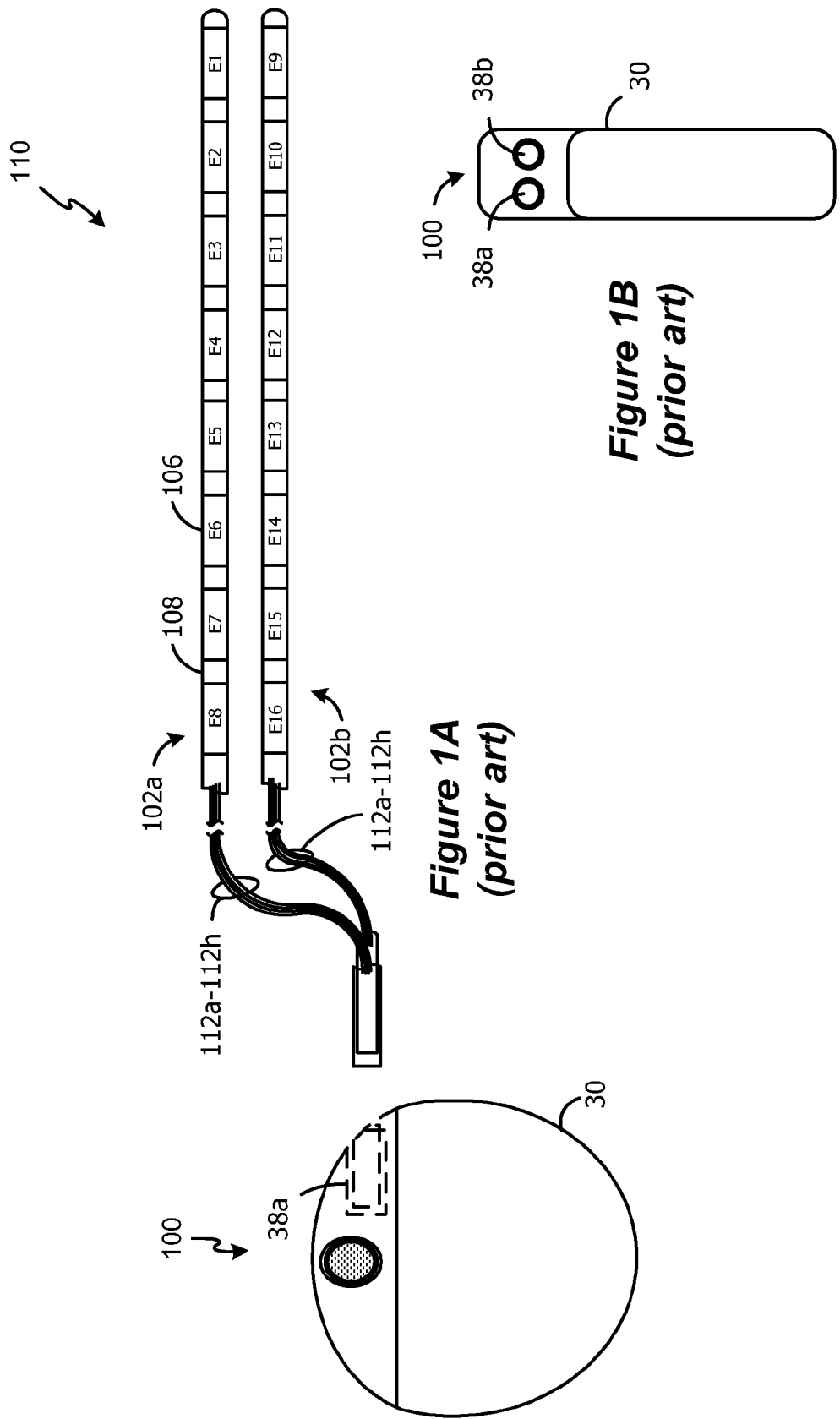
FIGS. 1A and 1B show an implantable pulse generator (IPG), and the manner in which an electrode array is coupled to the IPG, in accordance with the prior art.

FIGS. 1A and 1B show the electrode array 110 and the manner in which it is coupled to the IPG 100. As shown, the electrode array 110 comprises first and second implantable leads 102a and 102b. Leads 102a and 102b are in-line leads, meaning that both consist of a plurality of in-line electrodes 106. The electrodes are carried on a flexible body 108. In the illustrated embodiment, there are eight electrodes on lead 102a, labeled $E_1$-$E_8$, and eight electrodes on lead 102b, labeled $E_9$-$E_{16}$. The actual number of leads and electrodes will, of course, vary according to the intended application and should not be understood to be limiting in any sense. As discussed above, leads 102a and 102b may be implanted into a desired location, such as adjacent to the patient's spinal column, through the use of an insertion needle or other conventional techniques.

Each of the electrodes 106 on lead 102a are electrically connected to the IPG 100 by a first signal wire bundle 112 that extends through, or is imbedded in, the associated flexible body 108. Similarly, each of the electrodes 106 on the lead 102b are electrically connected to the IPG 100 by a signal wire bundle 112. Individual signal wires within the signal wire bundles connect with each electrode in the array (one such bundle of individual wires 112a-112h is shown in FIG. 1A).

The leads 102a and 102b and/or the lead extension 120 are connected to the IPG 100 by way of an interface. The interface may be any suitable device that allows the leads 102a and 102b and/or lead extension 120 to be removably connected to the IPG 100. The interface may comprise, for example, an electro-mechanical connector arrangement including lead connectors 38a and 38b. Alternatively, the leads 102a and 102b can share a single connector that mates with a corresponding connector on the IPG 100. Exemplary connector arrangements are disclosed in U.S. Pat. Nos. 6,609,029 and 6,741,892. Although the electrode array is shown as having two in-line leads 102a, 102b each with a plurality of electrodes 106 (e.g., eight each), it should be understood that more or fewer leads could be used. For example, a single in-line lead with 16 linearly-arranged electrodes 106 could be used as well.

Figure 2:
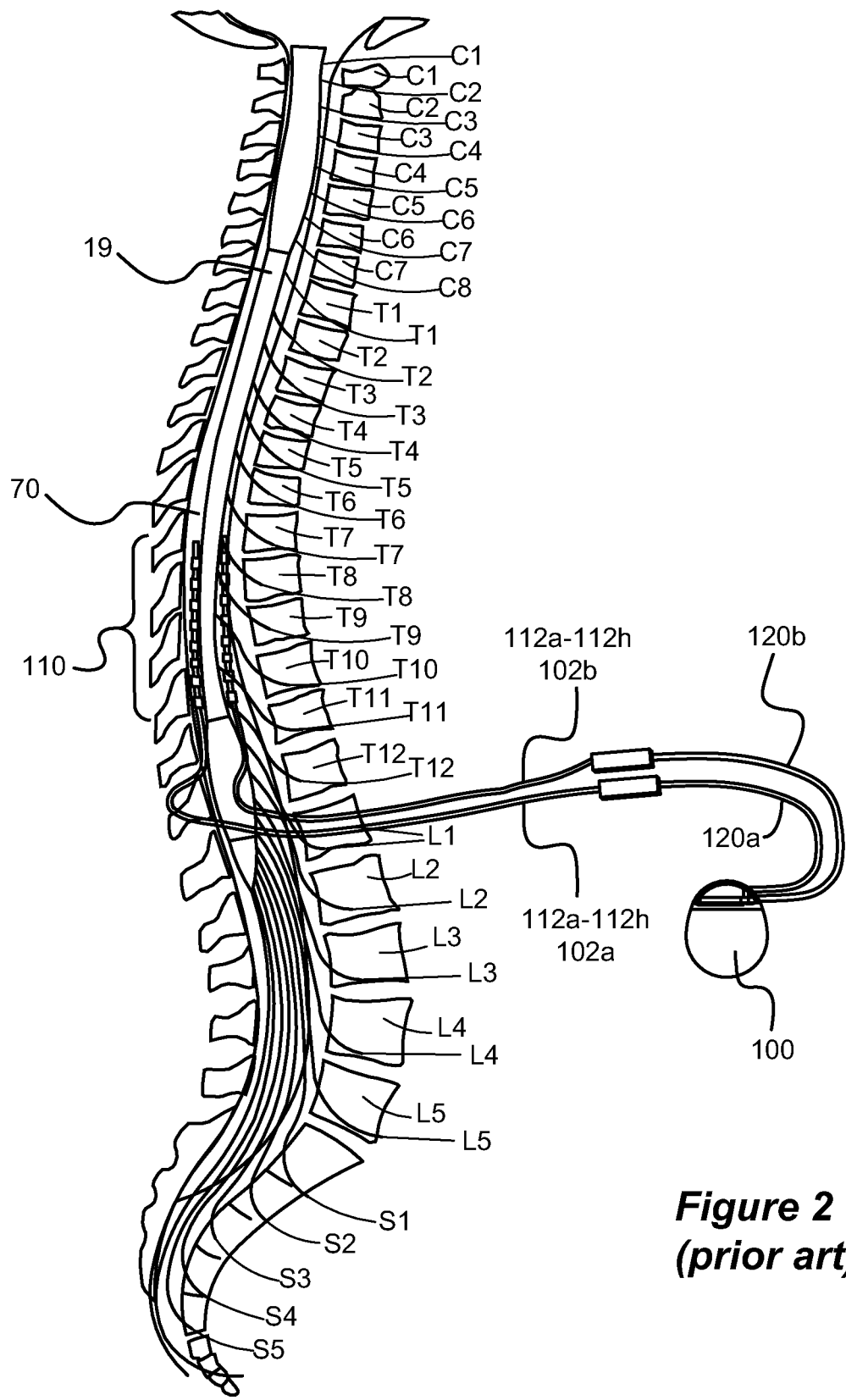
FIG. 2 shows the placement of the percutaneous leads for spinal cord stimulation with an in-line electrode array inserted alongside the spinal cord in the epidural space, in close proximity to the dura mater, in accordance with the prior art.

Turning to FIG. 2, an implantable pulse generator (IPG) 100, an electrode array 110, and (as needed) a lead extension 120 are shown in the context of being implanted in the human body. Typically, the IPG 100 is placed in a surgically-made pocket either in the abdomen, or just at the top of the buttocks. It may, of course, also be implanted in other locations of the patient's body. Once implanted, the IPG 100 is detachably connected to the lead system, comprising the lead extension 120, if needed, and the electrode array 110. The electrode array 110 and its leads 102a and 102b and/or extensions lead extensions 120, for example, may be tunneled up to the spinal column, such as in the epidural space next to the spinal cord 19, as shown in FIG. 2. Once implanted, the patient is ready for the trial stimulation phase to begin.

Figure 3:
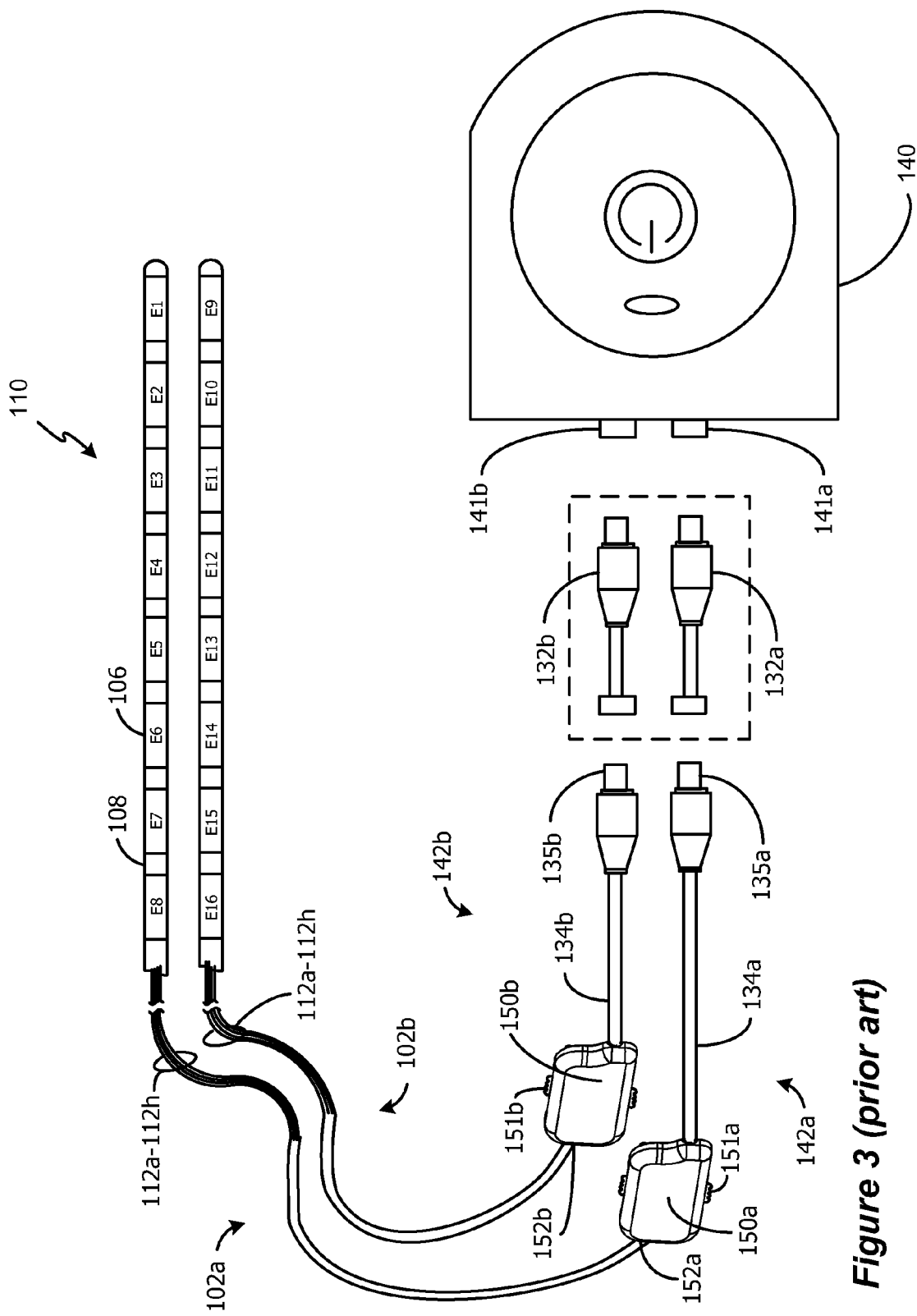
FIG. 3 shows one embodiment of an electrical stimulation system suitable for a trial stimulation period, the electrical stimulation system including one or more leads configured and arranged to electrically couple to an ETS via an external cable box assembly and, optionally, one or more trial stimulation cable extensions, in accordance with the prior art.

FIG. 3 shows a typical prior art ETS 140 and external cable box assembly 142 with associated leads 102a and 102b. The ETS 140 typically includes the same or similar pulse generation circuitry as does the IPG 100, and is used on a trial basis, e.g., for 7-10 days, after the electrode array 110 has been implanted and prior to implantation of the IPG 100, to test the effectiveness of the stimulation that is to be provided. During a trial stimulation phase, a patient is typically able to make adjustments to received stimulation.

For example, a patient may be able to turn the stimulation on and off, or adjust one or more stimulation parameters, such as stimulation amplitude, or switch between two or more different pre-programmed stimulation patterns, as desired. In at least some embodiments, a patient may be able to make stimulation adjustments using a remote control.

During a trial stimulation phase, the distal ends of leads 102a and 102b are implanted into the patient at a selected location, while the proximal end of the leads are electrically coupled to the ETS 140 via the external cable box assembly 142 (and, optionally, one or more trial stimulation cable extensions 132).

The leads 102a and 102b are inserted into opening 152 of external cable box 150. Sliding clamp 151 is used to connect and release the leads 102a and 102b from external cable box 150. As will be explained in greater detail below, pulling the sliding clamp 151 towards opening 152 will cause external cable box 150 to clamp down on the lead and create an electrical connection between the lead and the external cable box 150. Pushing the sliding clamp 151 away from opening 152 will release the lead and allow it to be removed from the external cable box 150.

External stimulation cables 134 extend from external cable box 150 and have male connectors 135 on their proximal ends. Male connector 135 is inserted into ETS ports 141 to establish electrical contact. External stimulation cables 134 electrically connect external cable boxes 150 to the ETS 140. External stimulation cables 134 contain signal wires 139 (shown in FIG. 5B) that transmit stimulation signals for each electrode 106 on the cable box 150's associated electrode lead 102a or 102b from the ETS 140 to the external cable box 150.

Figure 4:
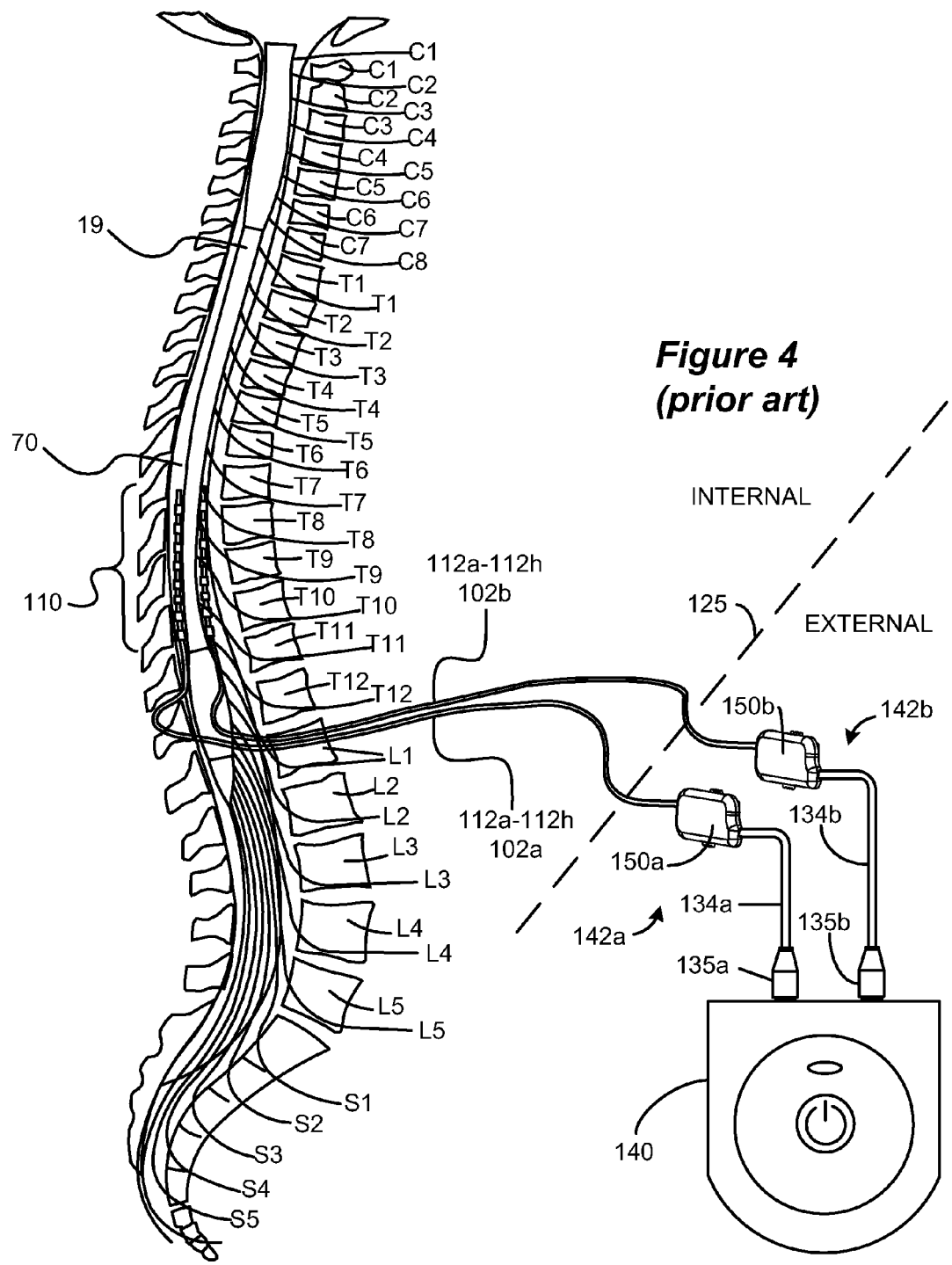
FIG. 4 shows the placement of the percutaneous leads during a trial phase of spinal cord stimulation with an in-line electrode array inserted alongside the spinal cord in the epidural space, in close proximity to the dura mater, in accordance with the prior art. The leads are electrically coupled to an ETS via an external cable box assembly.

FIG. 4 is a schematic view of one embodiment of an electrical stimulation system suitable for performing a trial stimulation phase on a patient. The electrical stimulation system includes one or more leads 102a, 102b, an external cable box assembly 142, and an ETS 140. In at least some embodiments, a distal end of the lead 102a, 102b is implanted into a patient so that a proximal end of the lead 102a, 102b remains external to the patient, as shown by dashed line 125 representing the internal/external interface of the patient. The proximal end of the lead 102a, 102b may be electrically coupled directly with the external cable box assembly 142 through opening 152.

In at least some alternate embodiments, the lead 102a, 102b may be entirely implanted into the patient and electrically coupled to a distal end of a lead extension 120 (not shown in FIG. 4) with a proximal end that remains external to the patient. Accordingly, in at least some embodiments the proximal end of the lead extension 120 may be electrically coupled to external cable box assembly 142 through opening 152. In at least some embodiments, an electrical stimulation system may also include other intermediate conductors, such as one or more additional lead extensions.

Electrical connectivity between the external cable box assembly 142 and the ETS 140 may, on occasion, become lost due to the external stimulation cables 134 becoming unplugged. Sometimes the patient may subsequently reconnect the external stimulation cables 134 (or trial stimulation cable extensions 132) to the incorrect ports 141 on the ETS 140 without knowing and accidently over-stimulate or incorrectly stimulate himself or herself. Insertion of an external trial stimulation cable 134 (or a trial stimulation cable extension 132) into the incorrect port 141 of an ETS 140 may also result in device performance degradation and even device failure.

Given these shortcomings, the art of implantable medical devices would benefit from an improved method for assuring the proper connection of external cables to an ETS. An improved device for assuring the proper connection of external cables is shown in FIGS. 5A and 5B.

Figure 5A:
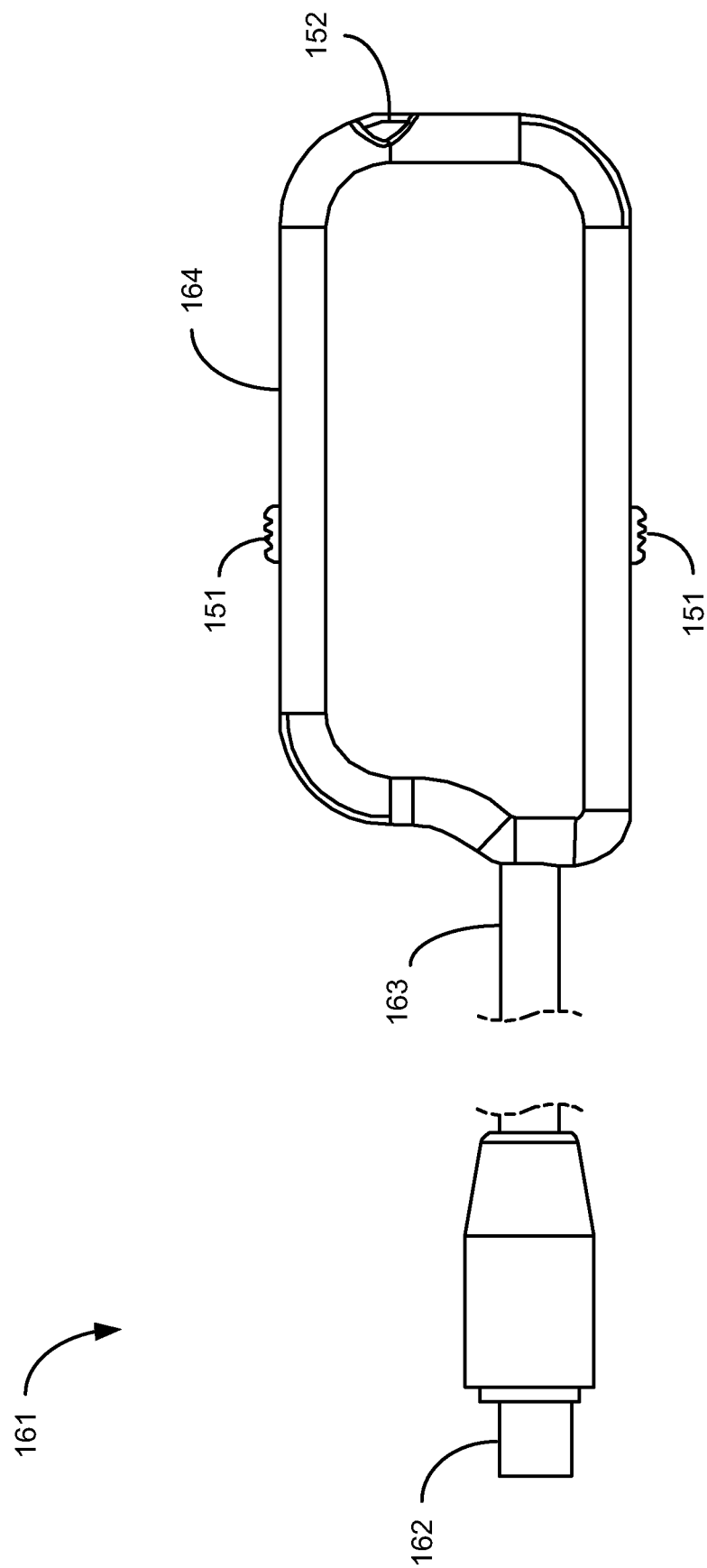
FIG. 5A shows a schematic view of the exterior of an improved external cable box assembly.

FIG. 5A shows one embodiment of an improved external cable box assembly 161. From the exterior, improved external cable box assembly 161 looks identical to prior art external cable box assemblies 142. However, improved cable box 164 possesses new memory circuitry 171 for identifying an address of the cable 161, as will be discussed below, that allows the cable box 164 to have a cable address that can be read and/or programmed by ETS 140. Further, external stimulation cable 163 and external stimulation cable male connector 162 contain additional wires 139 that transmit data and/or power from the ETS 140 to the external cable box 164, as will be explained further below. External stimulation cable 163 may also optionally contain a ground shield. All the mechanical elements of the improved external cable box assembly 161 described below are well known in the art, and thus are explained only briefly here.

Figure 5B:
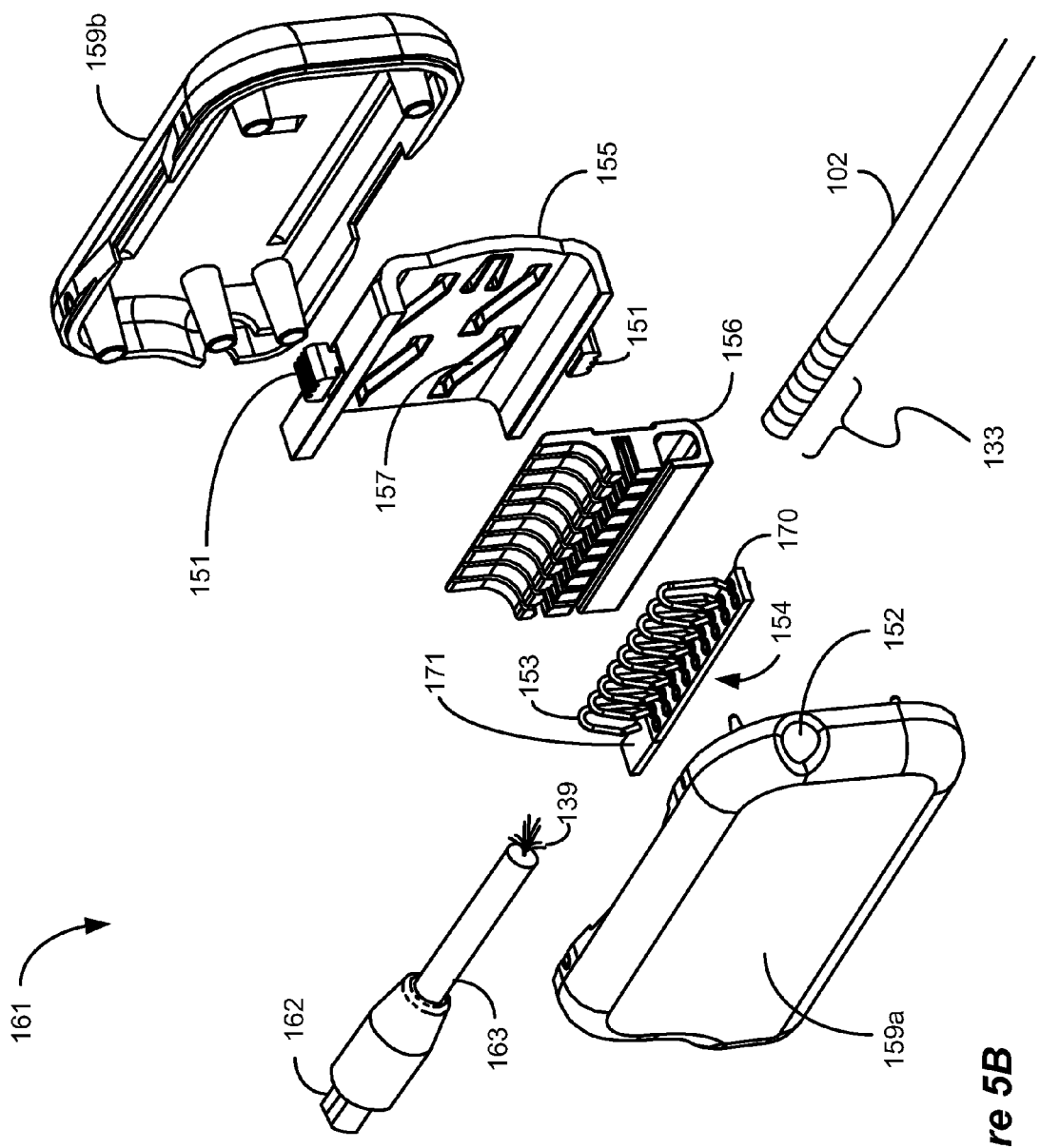
FIG. 5B shows a schematic exploded view of the improved external cable box assembly of FIG. 5A.

FIG. 5B shows a schematic exploded view of one embodiment of the improved external cable box assembly of FIG. 5A 161. The exterior of external cable box 164 consists of two housing pieces, 159a and 159b. These housing pieces 159 snap together and house the elements of the external cable box 164 which will be described below. The individual signal wires 139 contained in the external stimulation cable 163 are soldered directly to printed circuit board 170. Some of the signal wires 139 ultimately couple to electrodes 106 at the distal end of electrode lead 102a or 102b. Signal wires 139 also provide a path for the ETS 140 to send and receive data to and from the external cable box 164, as described further below. Optionally, one of the signal wires 139 may also be used to power the memory circuitry 171 on printed circuit board 170, which circuitry is discussed further below.

Nine individual pin connectors 153 are mounted on printed circuit board 170 forming a pin connector array 154. Eight of the pin connectors 153 electrically connect to the conductive contacts 133 on the proximal end of lead 102 when lead 102 is clamped into the cable box 164. Each pin connector 153 represents one of the electrodes 106 on the implanted lead 102. In this way, the information regarding the manner (e.g., strength, duration, frequency, mode) in which each of the electrodes 106 is stimulated is transferred from the ETS 140 to the lead 102 that is implanted in the patient. The ETS 140 may likewise sense or read feedback information from the electrodes 106. The ninth pin connector serves as an optional extra electrode connector. The number of pin connectors 153 is not limited, and can vary to accommodate any number of electrodes 106 on the implanted lead 102.

The pin connector array 154 is slid into, and held in place by, printed circuit board holder 156. On the rear side of printed circuit board holder 156 are four rectangular protrusions (not shown) which fit into the sliding rail tracks 157 on the external cable box's slide actuator 155. As discussed above, sliding clamp 151 is used to connect and release the lead 102 from the external cable box 164. Pulling the sliding clamp 151 towards opening 152 will cause the protrusions on the rear side of printed circuit board holder 156 to travel along the sliding rail tracks 157, thus raising printed circuit board holder 156 in relation to the cable box 164. As printed circuit board holder 156 rises, pin connector array 154 also rises, causing each of the pin connectors 153 to clamp down on the lead 102 and create electrical connections between the pin connectors 153 and the lead's conductive contacts 133. Pushing the sliding clamp 151 away from opening 152 will have the opposite effect mechanically, causing printed circuit board holder 156 to lower in relation to the cable box 164, thereby releasing the pin connector array 154 from the lead 102, and allowing lead 102 to be removed from the cable box 164 by pulling it back out through opening 152. This exemplary external cable box embodiment should not be deemed to be limiting, as many other possible mechanisms and types of electrical connections could achieve similar functionality.

Figure 6A:
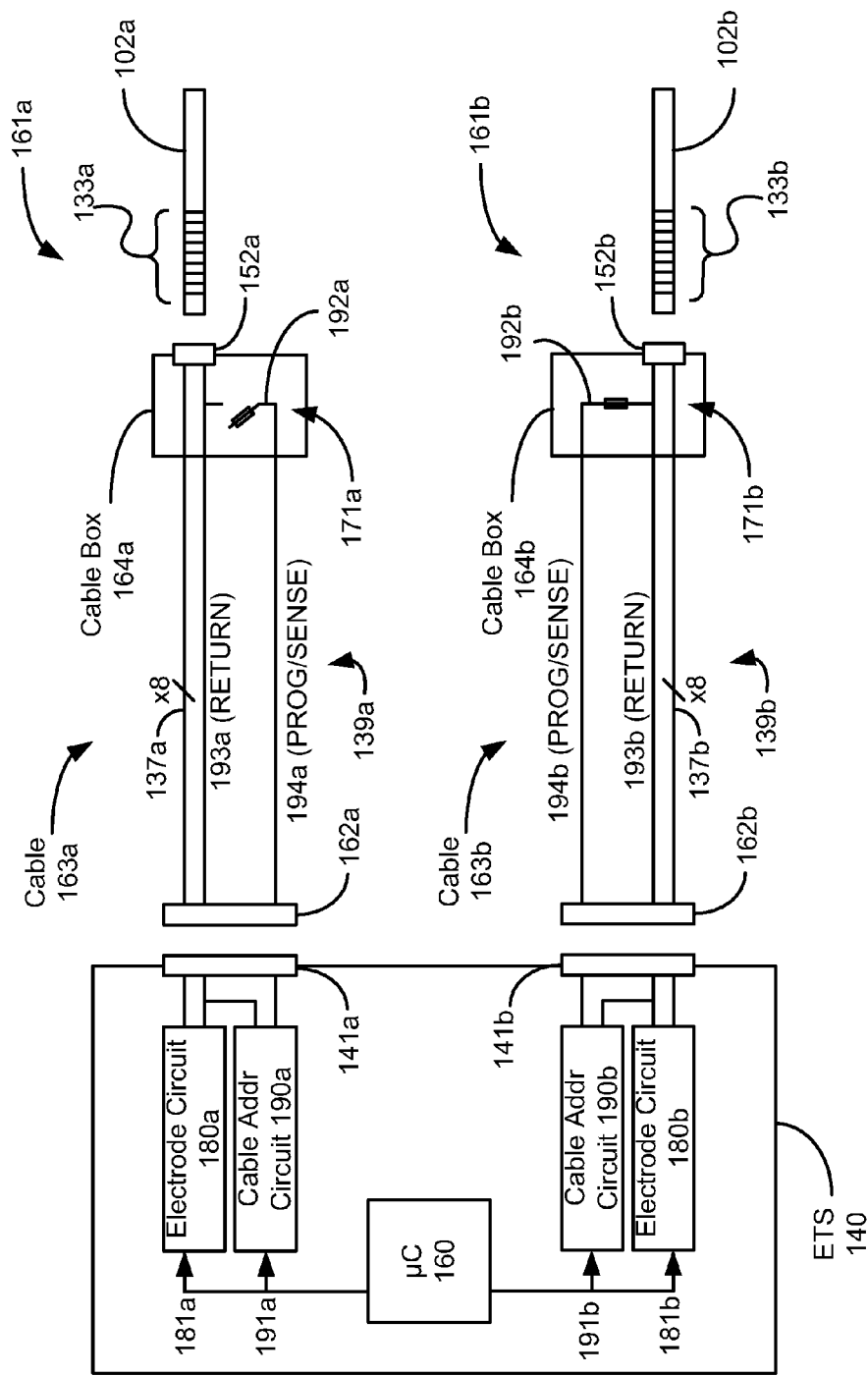
FIG. 6A shows a schematic view of an ETS and one embodiment of an improved external cable box assembly.

FIG. 6A shows a high-level schematic view of an ETS 140 and one embodiment of an improved external cable box assembly 161. The ETS 140's microcontroller 160 typically comprises a microprocessor and associated logic circuitry, which in combination with control logic circuits, timer logic, and an oscillator and clock circuit, generate the necessary control and status signals to allow the microcontroller 160 to control the operation of the ETS 140 in accordance with a selected operating program and stimulation parameters. In this embodiment, the memory circuitry 171 used to identify the external cable box assembly 161 consists of a simple fuse circuit 192. Fuse 192a is shown in a blown or "open" position, and fuse 192b is shown in a not blown or "closed" position for illustrative purposes only. Either cable box 164a or 164b could possess the fuse that has been blown. There is also cable addressing circuitry 190 in the ETS 140 to program and sense the state of the fuse 192. Alternately, an antifuse could be used in circuit 192 to achieve similar functionality. Cable addressing circuitry 190 is explained in greater detail below in relation to FIG. 6B.

If an external stimulation cable 163a is plugged into port 141a and microcontroller 160 has previously assigned a cable address 165a (FIG. 10) to port 141a, microcontroller 160 sends an enabling signal 191a to the cable addressing circuitry 190a instructing the cable addressing circuitry 190a to sense the status of the external cable box's fuse 192a over program/sense line 194a. Return line 193a allows a return path for the current. In one embodiment, if the external cable box's fuse 192a has been blown, the address of the external cable box will return a '1' to microcontroller 160. If the external cable box's fuse 192a has not been blown, the address of the external cable box will return a '0' to microcontroller 160. Alternately, an address of '0' could be used for the cable box with the blown fuse, and an address of '1' could be used for the cable box with the not-blown fuse.

Microcontroller 160 will then compare the cable address returned to it with the cable box address 165a that it has stored for port 141a. If there is match between the cable address 165a and the cable address of the cable box 164a, the microcontroller 160 determines that the cable 163a is connected to the correct port 141a and sends an enabling signal 181a to the electrode stimulation circuitry 180a, which delivers the appropriate electrical stimulation therapy program 168 over the electrode signal wires 137a.

If instead, the cable address 165a that the microcontroller 160 has stored for port 141a and the cable address of the cable box 164a do not match, microcontroller 160 determines that the cable 163a is not connected to the correct port 141a. The microcontroller 160 may then alert the patient via an appropriate visual, auditory, tactile, or other cue that the cable 163a has been plugged into the incorrect port 141a. For example, the ETS 140 might emit an audible beep, cause an LED light to flash, display a simple message, or vibrate to alert the patient of an incorrect connection. Alternatively, the microcontroller 160 may simply reroute the correct stored electrical stimulation therapy program 168 (i.e., the stored electrical stimulation therapy program that is associated with the cable box 164a presently connected to port 141a), as is shown in further detail in FIG. 10. In this way, the delivery of the correct therapy to the patient is seamless, and requires no interaction from the patient.

If an external stimulation cable 163a is plugged into port 141a and microcontroller 160 has not previously assigned a cable box address 165a to port 141a, microcontroller 160 sends an enabling signal 191a to the cable addressing circuitry 190a instructing the cable addressing circuitry 190a to program the external cable box's fuse 192a over program/sense line 194a. Microcontroller 160 then decides whether it wants the current port, here 141a, which will be associated with the external cable box 164a, to have a blown or not-blown fuse.

If the microcontroller 160 determines that the external cable box 164a currently plugged into port 141a should have a blown fuse, cable addressing circuit 190a sends out a current to fuse 192a over program/sense line 194a that is sufficient to blow the fuse, essentially creating an open circuit in cable box 164a. Microcontroller 160 will then store a cable address 165a of '1' for port 141a. Cable box 164a will then return an address of '1' any time that cable addressing circuitry 190a queries cable box 164a's address.

If instead, the microcontroller 160 determines that the external cable box 164a currently plugged into its port 141a should be the cable box with the fuse that is not blown, microcontroller 160 will simply store an address 165a of '0' for port 141a. Cable box 164a will then return an address of '0' any time that cable addressing circuitry 190a queries cable box 164a's address.

In this embodiment, microcontroller 160 possesses logic such that it will only assign cable addresses 165 to its ports 141 once, and it will also ensure that one port 141 is always assigned to a cable box address 165 of '0' and the other port is assigned to a cable box address 165 of '1.' In this way, the ETS 140 is able to identify each external cable box assembly 161 and ensure that the appropriate electrical stimulation therapy program 168 is sent out to each of its ports 141.

Figure 6B:
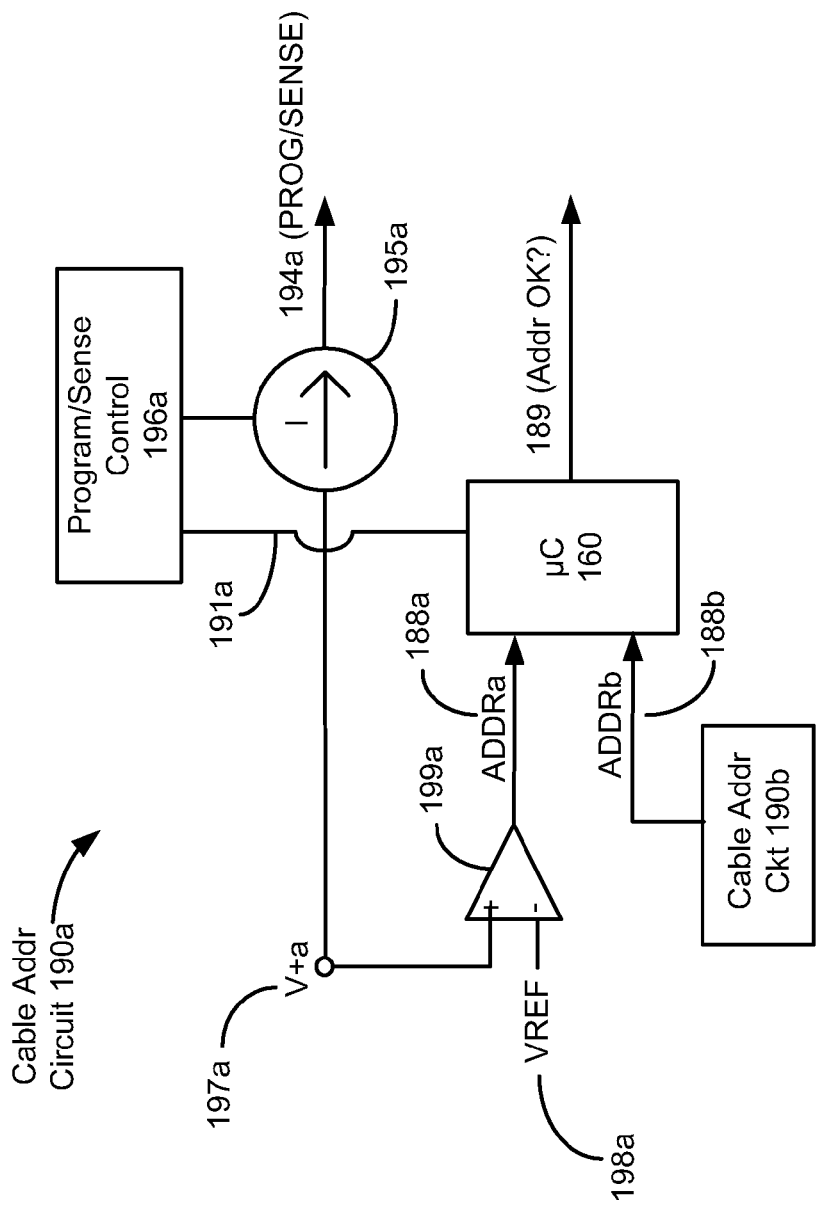
FIG. 6B shows the cable addressing circuitry of the ETS shown in FIG. 6A.

Turning to FIG. 6B, the cable addressing circuit 190 within the ETS 140 is explained in further detail. Program/Sense Control circuit 196 causes current source generator 195 to generate a current in response to receiving a program or sense command over the cable addressing circuit enabling signal line 191a. If Program/Sense Control circuit 196 receives a command to program the external cable box 164's fuse 192, it causes current source generator 195 to generate a program current sufficient to blow the fuse 192 in external cable box 164. If instead, Program/Sense Control circuit 196 receives a command to sense the external cable box 164's fuse 192 status, it causes current source generator 195 to generate a smaller sense current that is not sufficient to blow fuse 192. To generate either current, the cable addressing circuitry 190 will use voltage 197, labeled V+.

When sensing, if the fuse 192 in external cable box 164 has been blown, V+ will rise to a relatively high level in an attempt to provide the proper amount of sense current through the blown fuse 192. As a result, the positive input of operational amplifier 199 will be higher than a reference voltage 198, VREF, at the negative input of operational amplifier 199, and address line 188 will output a high signal, or an address of '1.'

If instead, the fuse 192 in external cable box 164 has not been blown, V+ need rise to a relatively small level to provide the sense current through the non-blown fuse 192. As a result, the positive input of operational amplifier 199 will be lower than the compliance voltage 198, labeled VREF, at the negative input of operational amplifier 199, and address line 188 will output a low signal, or an address of '0.'

Whenever an external cable assembly 161 is re-plugged into ETS 140 after the ETS 140 has already stored cable box addresses 165 for each of its ports 141, microcontroller 160 sends out signals requesting that both ports' cable addressing circuitry 190 sense the status of its external cable box assembly's fuse 192. Microcontroller 160 will receive the addresses of the two external cable box assemblies, 188*a* and 188*b*, and compare each address to the address 165*a* and 165*b* that it has stored in memory for each cable's port 141. If the cable addresses 188 for each port match the values the microcontroller 160 has stored in memory for its ports, microcontroller 160 reports an "Addresses OK" signal 189. If the cable addresses sensed for each port do not match the cable addresses 165 that the microcontroller 160 has stored in memory for its ports, microcontroller 160 reports an "Addresses not OK" signal 189. At this point, the ETS 140 will either alert the patient to swap the port locations of the external stimulation cables 163, or the ETS 140 will automatically reroute the correct electrical stimulation therapy program 168 through each port 141, as will be explained further below.

Figure 7:
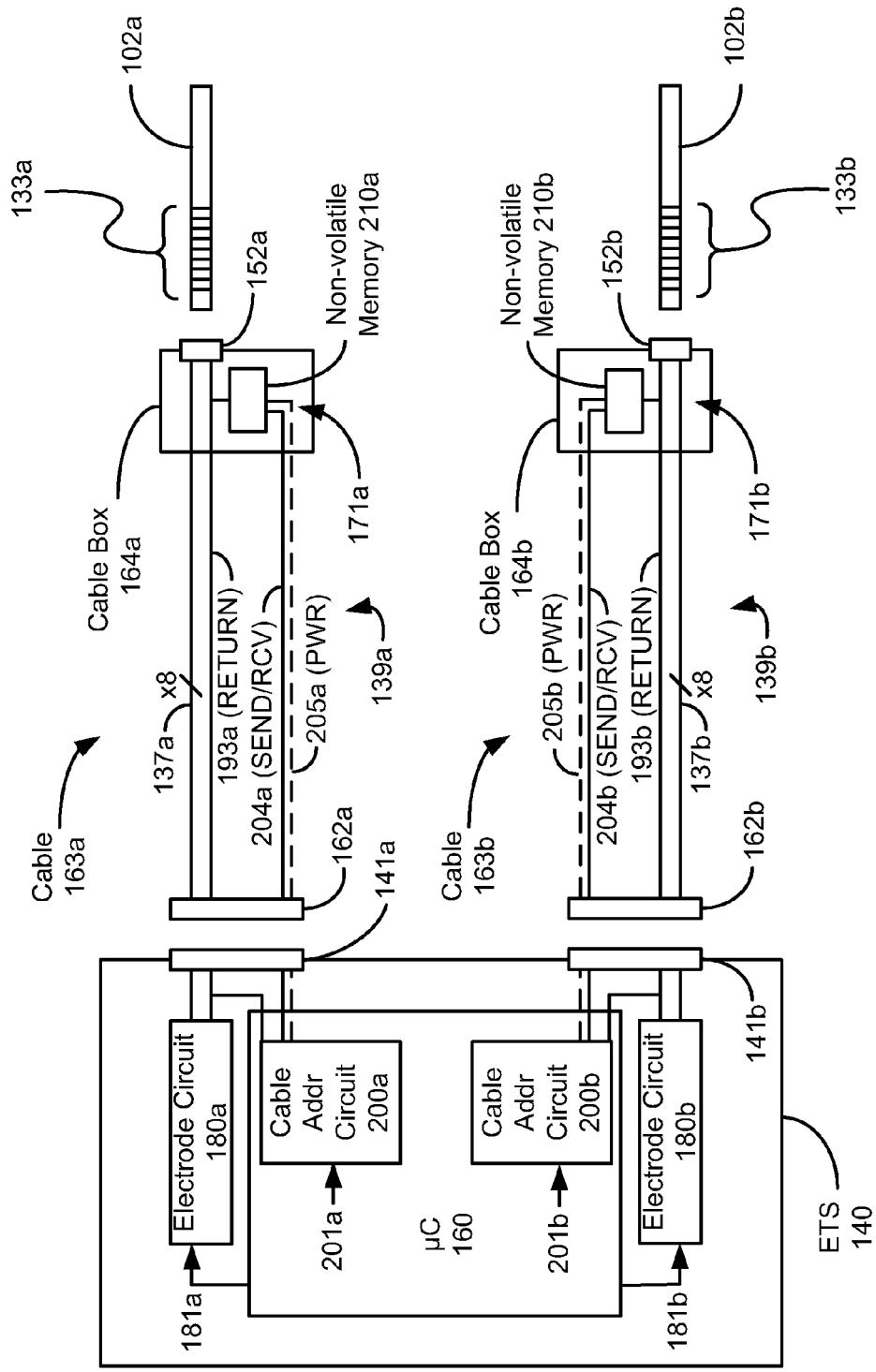
FIG. 7 shows a schematic view of a second embodiment of an ETS and one embodiment of an improved external cable box assembly.

FIG. 7 shows a high-level schematic view of an ETS 140 and another embodiment of an improved external cable box 164. In this embodiment, the memory circuitry 171 used to identify the external cable box assembly comprises a non-volatile memory circuit 210, which could be implemented with, for example, flash memory or EEPROM. Cable addressing circuitry 200, which may be implemented by the external trial stimulator's microcontroller 160, sends and receives information from the non-volatile memory circuit 210 to program and sense its address.

In the embodiment shown in FIG. 7, when external stimulation cables 163 are plugged into ETS 140, microcontroller 160 checks to see if cable addresses 165 have been assigned to each port 141 by sending an enabling signal 201 to the cable addressing circuitry 200. If cable addresses 165 have already been assigned to each port 141, the cable addressing circuitry 200 sends a "read" signal over Send/Receive line 204. This request causes the non-volatile memory circuit 210 in the external cable box 164 to return its programmed cable address to the cable addressing circuitry 200. Microcontroller 160 then compares the cable address returned by each non-volatile memory circuit 210*a* and 210*b* to the addresses 165*a* and 165*b* that it has stored in memory. If the cable addresses returned to the cable addressing circuitry 200 match the stored cable addresses 165 for each port 141, microcontroller 160 continues to deliver the electrical stimulation therapy program 168 as it did before the external stimulation cables 163 were unplugged. If the cable addresses returned to the cable addressing circuitry 200 do not match the stored cable addresses 165 for each port 141, microcontroller 160 either alerts the patient to swap the port locations of the external stimulation cables 163, or the ETS 140 automatically reroutes the correct electrical stimulation therapy program 168 through each port 141.

If instead, when external stimulation cables 163 are plugged into ETS 140, microcontroller 160 determines that cable addresses 165 have not already been assigned to each port 141, the cable addressing circuitry 200 sends a preliminary "read" signal over Send/Receive line 204 to determine if non-volatile memory circuit 210 has any address value stored therein. If cable addressing circuitry 200 returns a non-null cable address value that is not equal to any already-stored cable address 165, microcontroller 160 simply stores that returned cable address value in memory as the cable address 165 for that port 141. If instead, cable addressing circuitry 200 returns a null value, microcontroller 160 generates a cable address and saves that value in memory as the cable address 165 for that port 141. Finally, microcontroller 160 issues a "write" command over Send/Receive line 204 and writes the newly-generated cable address to the non-volatile memory circuit 210 of the external cable box 164.

Dedicated power line 205 is shown as a dashed line to represent that it is optionally one of the signal wires 139 bundled in improved external stimulation cable 163. If power line 205 is present, it is used to send power from the ETS 140 to external cable box 164 to power the non-volatile memory circuitry 210. If optional power line 205 is not present, external cable box 164 needs some other internal power source (such as a battery cell; not shown) to power its non-volatile memory circuitry 210.

Figure 8A:
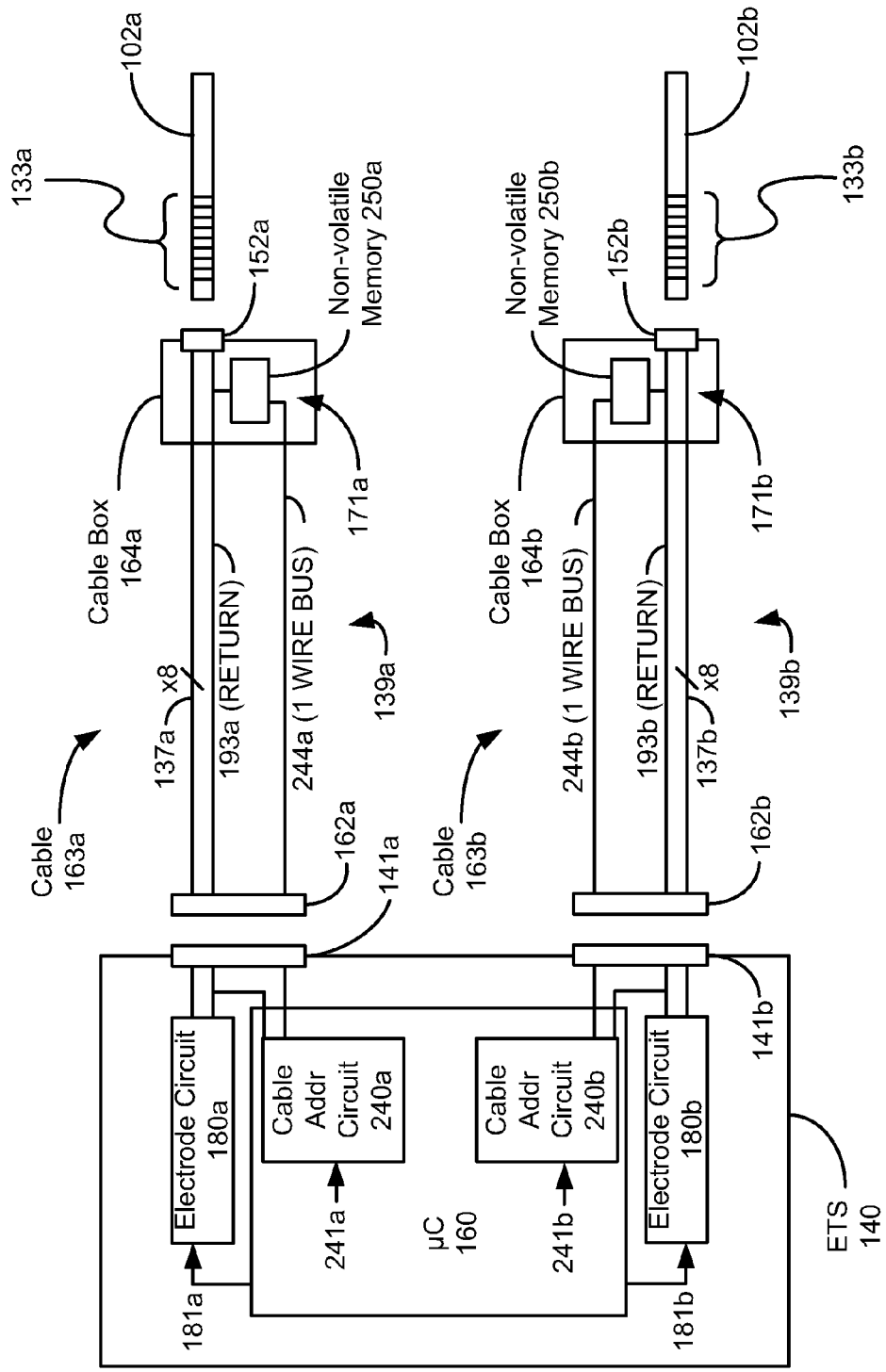
FIG. 8A shows a schematic view of a third embodiment of an ETS and an improved external cable box assembly.

FIG. 8A shows a schematic view of an ETS 140 and another embodiment of an improved external cable box 164. In this embodiment, the memory circuitry 171 used to identify the external cable box assembly 161 consists of a memory circuit 250, such as a Maxim 1-WIRE® memory circuit. There is also associated cable addressing circuitry 240 in the ETS's microcontroller 160 that responds to an enabling signal 241 by reading the unique, factory-programmed address stored in the memory circuit 250 and returning that value to microcontroller 160.

Memory circuit 250 provides a unique and unalterable, factory-programmed ID in each device (in the Maxim 1-WIRE®) memory circuit, a 64-bit ID). One advantage of using Maxim 1-WIRE®) memory circuit 250 is that the external cable box 164 is "parasitically" powered by the same wire 244 when data is sent to or read from the non-volatile memory circuit 250. Therefore, a discrete power supply wire is not needed to achieve the improved external cable box assembly functionality of the present invention, thus simplifying the design.

In the embodiment shown in FIG. 8A, when external stimulation cables 163 are plugged into ETS 140, and microcontroller 160 determines cable addresses 165 have already been assigned to each port 141, the "read" functionality carried out by ETS 140 is identical to the "read" functionality described in relation to the embodiment shown in FIG. 7. However, when external stimulation cables 163 are plugged into ETS 140, and microcontroller 160 determines that cable addresses 165 have not already been assigned to each port 141, the cable addressing circuitry 240 sends a "read" signal over Send/Receive line 244 to return non-volatile memory circuit 250's factory pre-programmed unique address and saves that cable address value in memory as the cable address 165 for that port 141. Because memory circuit 250 comes from the factory with a pre-programmed unique address, the need for microcontroller 160 to: (a) check whether or not the cable box's memory has ever been programmed; (b) generate cable addresses; and (c) program the non-volatile memory circuit of the external cable box—each of which is required by the embodiment shown in FIG. 7—is eliminated.

Figure 8B:
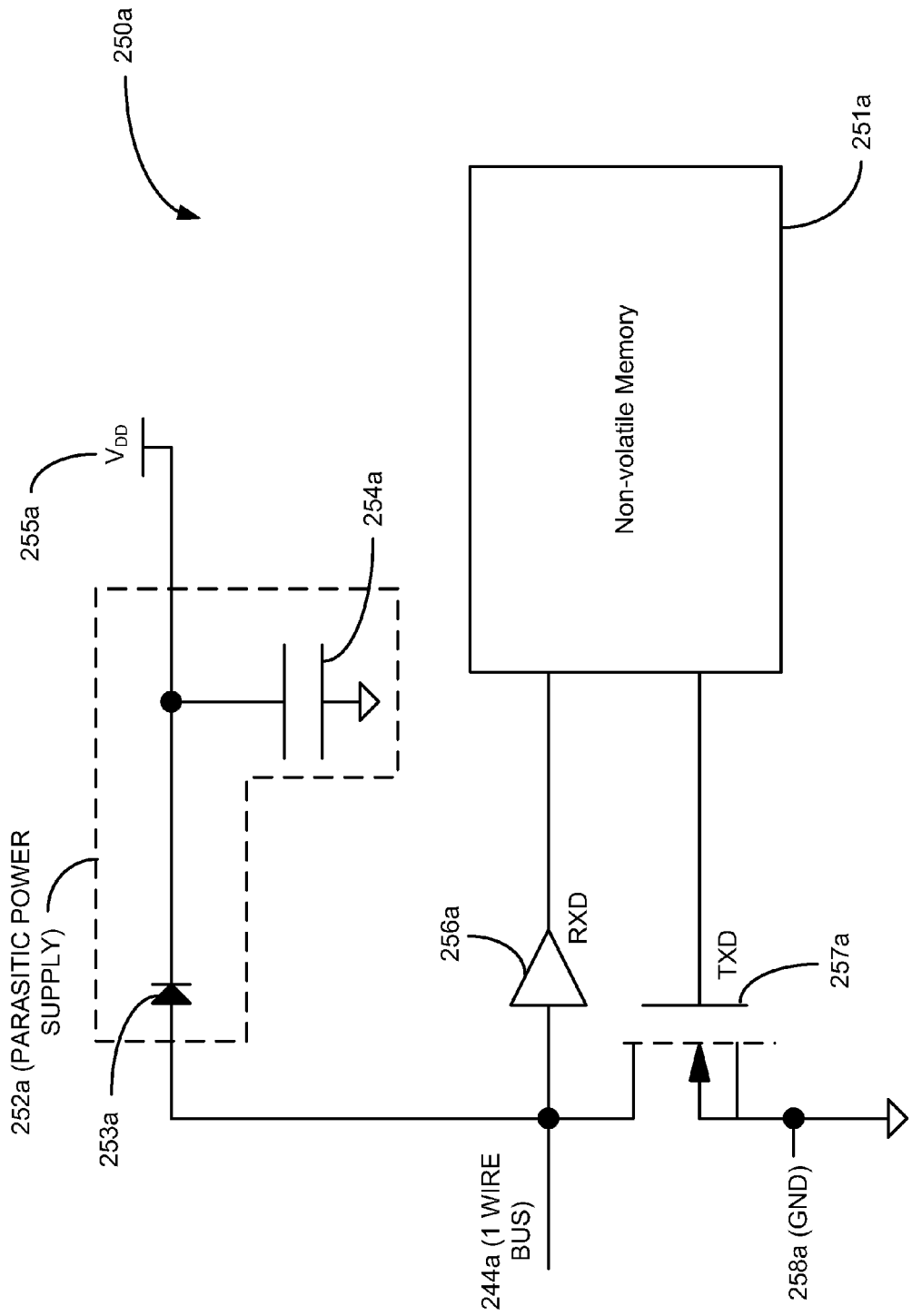
FIG. 8B shows the external cable box circuitry used in conjunction with the embodiment shown in FIG. 8A.

As is shown in FIG. 8B, a Maxim 1-Wire® memory circuit 250 includes: (a) a parasitic power supply 252, made up of diode 253 and capacitor 254; (b) an internal voltage source 255; (c) receiver 256; (d) a transmitter 257; (e) a ground reference 258; and (f) memory 251 and its associated drivers. The 1-WIRE® memory circuit 250 uses a serial protocol, using a single data line 244 plus a ground reference 258 for communication. Again, power for the memory circuit 250 is derived parasitically, and thus a separate power line is not required.

Further description of Maxim 1-WIRE®) products can be found in Maxim Application Note 1796, entitled, "Overview of 1-Wire® Technology and Its Use," available for download at http://pdfserv.maxim-ic.com/en/an/AN1796.pdf, and submitted in the information disclosure Statement filed herewith. This document is hereby incorporated by reference in its entirety.

Figure 9:
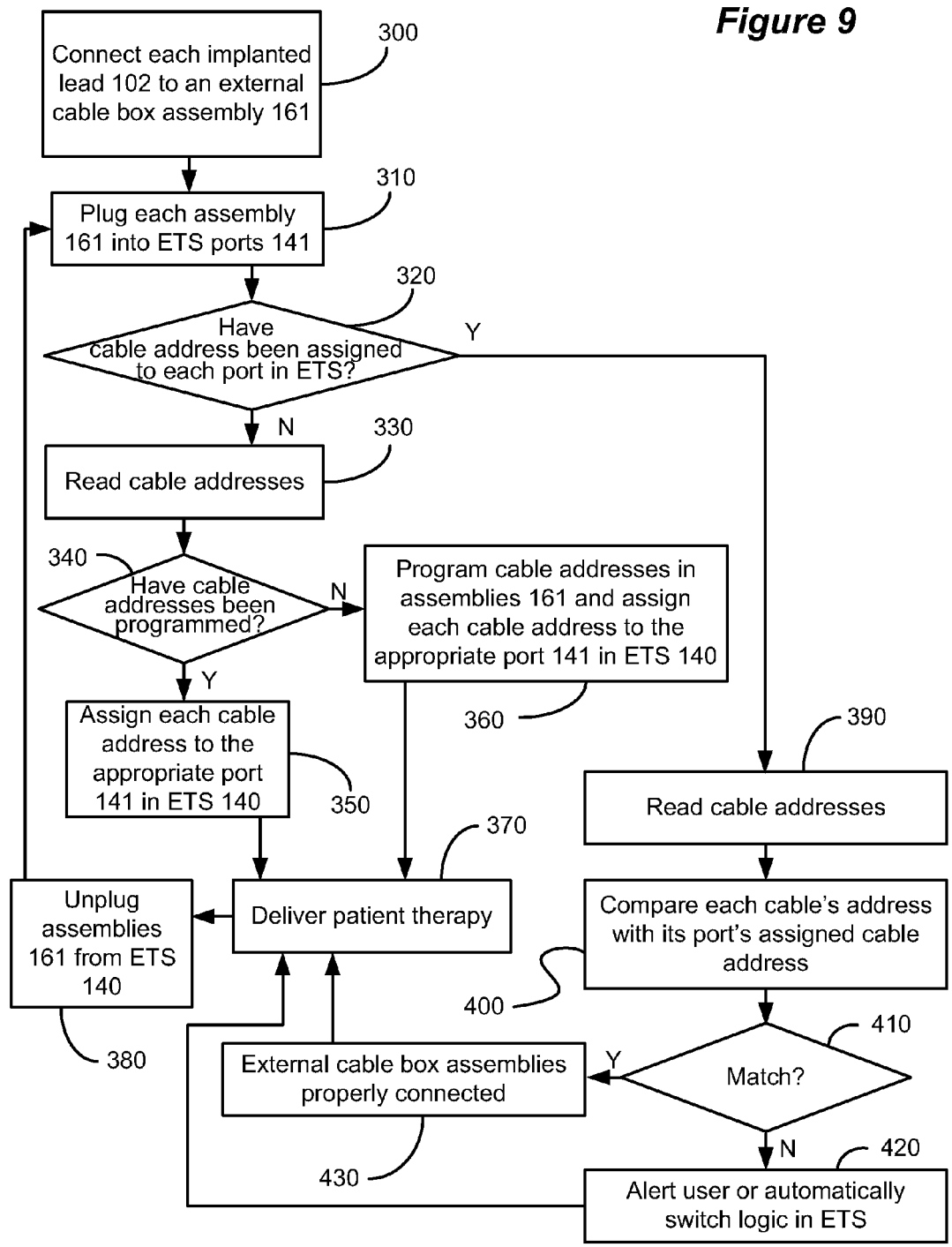
FIG. 9 is a flowchart detailing one embodiment of a technique for assuring the proper connection of external cables to an ETS.

Turning now to FIG. 9, a flowchart detailing one embodiment of a technique for assuring the proper connection of external cables to an ETS is described in further detail. First, each implanted lead 102 is connected to an external cable box assembly 161 (300). Then, each external cable box assembly 161 is plugged into an ETS port 141 (310). Next, the ETS 140 determines whether cable addresses 165 have been assigned to each port 141 (320). If cable addresses 165 have already been assigned to each port, ETS 140 reads the cable addresses of the external cable box assemblies 161 currently plugged into ETS 140 (390) and compares each of those cable addresses with the cable addresses 165 stored in the memory of microcontroller 160 (400). If the cable addresses 165 assigned to each port 141 match the addresses of the cable box assemblies 161 plugged into the ETS ports (410), ETS 140 determines that the external cable box assemblies 161 are properly connected (430), and the proper electrical stimulation therapy program 168 is delivered to the patient (370). If the cable addresses 165 assigned to each port 141 do not match the addresses of the cable box assemblies 161 plugged into the ETS ports (410), ETS 140 determines that the external cable box assemblies 161 are not properly connected, and the ETS 140 alerts the user of the error or, in some embodiments, automatically reroutes the correct electrical stimulation therapy program 168 through the correct ETS port 141 if possible (420). If it is possible to reroute the correct electrical stimulation therapy program 168 through the correct ETS port 141, the proper electrical stimulation therapy will resume being delivered to the patient (370).

If, when external stimulation cables 163 are plugged into ETS 140, the ETS 140 determines that cable addresses 165 have not yet been assigned to each port 141 (320), the ETS attempts to read the cable address of each external cable box assembly 161 (330). Subsequently, if the cable addresses of each external cable box assembly 161 are found to be equal to each other (or if either cable address is equal to some predetermined null value indicating that its address has never been programmed) (340), the ETS 140 will know that it needs to program cable addresses into each external cable box assembly 161 and assign each of the newly-programmed cable addresses 165 to the appropriate port 141 in ETS 140 (360). This might be the case if the cable assemblies 161 are implemented with fuses 192 (FIG. 6A) or a general purpose non-volatile memory 210 (FIG. 7), for example. If the ETS instead finds that the cable addresses of each external cable box assembly 161 are not equal to each other (and are not equal to the predetermined null value) (340), the ETS will know that the external cable box assemblies 161 came with a factory-programmed unique address, and that all the ETS 140 needs to do is assign each of the currently plugged in cable assembly 161's addresses to the port 141 of ETS 140 that the cable assembly 161 is currently plugged into (350). Once cable addresses 165 have initially been assigned to each port 141 of ETS 140 in the memory of microcontroller 160, the proper electrical stimulation therapy program 168 is delivered to the patient (370).

If, at any point in time, the external cable assemblies 161 become unplugged from ETS 140 (380), and are subsequently re-plugged into ETS 140 by the patient or physician (310), the logic in ETS 140, as depicted in FIG. 9, can repeat by reading the cable addresses (390), comparing (400), etc. If no match is determined (410), the ETS 140 ensures that the patient continues to receive the correct electrical stimulation therapy program 168 by either (a) alerting the patient that external stimulation cables 163 were re-plugged into different ports 141 on ETS 140 than they were initially plugged into; or (b) automatically rerouting the correct electrical stimulation therapy program 168 through the correct ETS port 141, as was described above (420). The steps and order of steps depicted in FIG. 9 are illustrative only and other steps and ordering of steps can be used.

Figure 10:
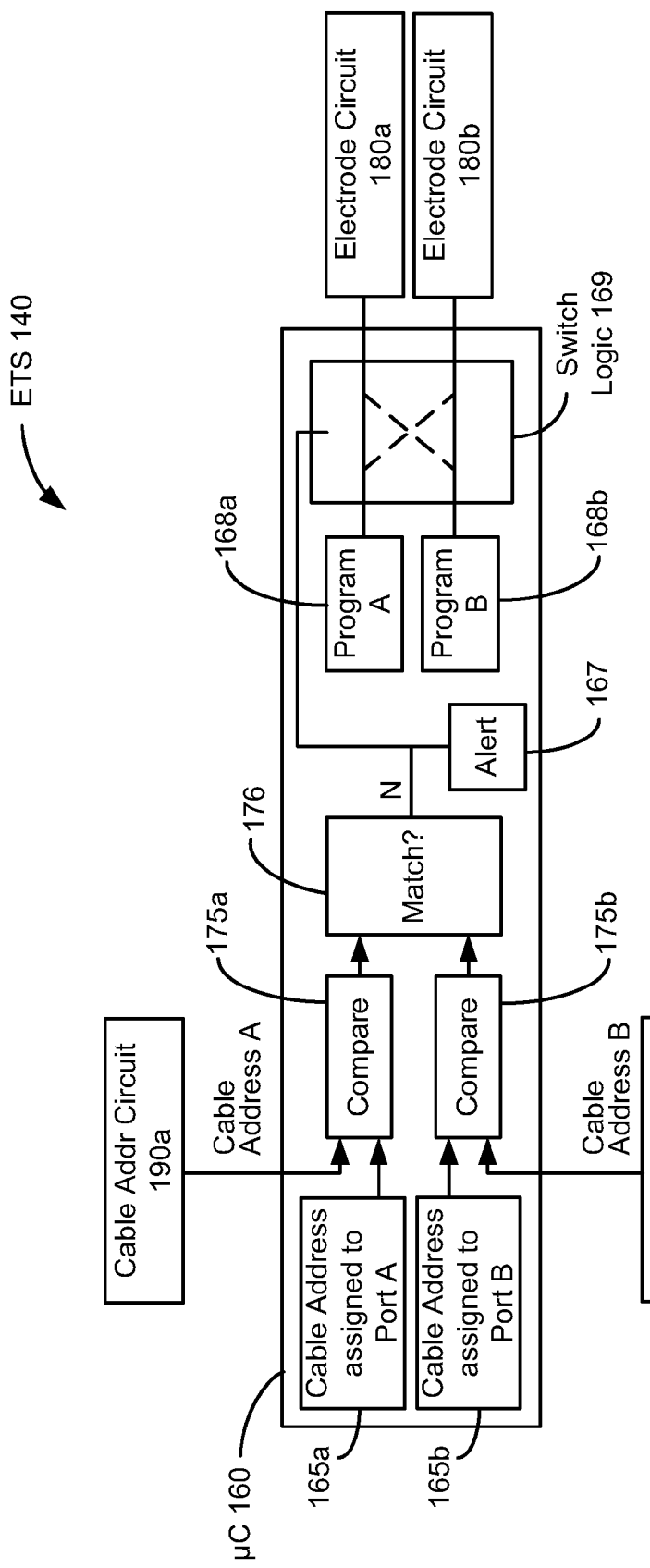
FIG. 10 is a high-level circuit schematic showing the basic logic carried out by the ETS's microcontroller when external stimulation cables are re-plugged into the ETS.

FIG. 10 is a circuit schematic disclosing the logic carried out by ETS 140 in performing the various steps of FIG. 9. In FIG. 10, cable addresses 165a and 165b have already been stored in the memory of microcontroller 160 and assigned to one of the ports 141a and 141b of ETS 140. Thus, when external stimulation cables 163 are re-plugged into ETS 140, microcontroller 160 enables its cable addressing circuitry 190 to read the address of each of the external cable box assemblies 161. It then compares the cable addresses returned from cable addressing circuitry 190 with the cable addresses 165 that it has stored in memory (175a and 175b) to determine if they match (176). If each cable address matches with the cable address 165 that is assigned to the port the cable is currently plugged into, microcontroller 160 directs the electrode stimulation circuitry 180 to deliver the electrical stimulation therapy program 168 to the patient as normal, such that Program A 168a is sent to port 141a on the ETS 140, and Program B 168b is sent to port 141b on the ETS. If instead, each cable address returned from cable addressing circuitry 190 does not match the cable address 165 that is assigned to the port the cable is currently plugged into, microcontroller 160 either alerts the user to the problem (167) or activates switch logic 169 to deliver the correct electrical stimulation therapy program to the patient. For example, if ETS 140 detects that external stimulation cables 163 have been re-plugged into the incorrect ports 141, it may activate switch logic 169 to deliver electrical stimulation therapy program A 168a to port B 141b and electrical stimulation therapy program B 168b to port A 141a. Switch logic 169 may be implemented via proper programming of the logic within the microcontroller 160 as shown, or may comprise discrete circuitry such as transistors, other suitable electrical switches, etc.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
    an external assembly, comprising:
        a first port configured to couple to a stimulation lead comprising at least one electrode for stimulating a patient's tissue,
        a cable terminating at a connector, and
        a first circuit comprising a first address of the external assembly; and an external trial stimulator, comprising:
a plurality of second ports each having a second address and configured to receive the connector, wherein the connector is configured to be attachable and detachable from the second ports by a user, and
control circuitry configured to:
initially associate the external assembly with one of the second ports by:
assigning the second address to the one of the second ports, and
programming the first address of the external assembly to match the second address of the one of the second ports,
read the first address and compare it to the second address of a second port to which the connector is attached, and
perform an action when the first address does not match the second address of the second port to which the connector is attached.

2. The system of claim 1, wherein the action comprises generating an alert to the user.

3. The system of claim 2, wherein the alert is visual or audible.

4. The system of claim 1, wherein the first circuit comprises a fuse or antifuse indicating the first address.

5. The system of claim 1, wherein the first circuit comprises a memory storing the first address.

6. The system of claim 1, wherein the external assembly comprises a box, wherein the box comprises the first port and the first circuit.

7. The system of claim 6, wherein the cable extends from the box and terminates at the connector.

8. The system of claim 1, wherein the external trial stimulator further comprises an electrical stimulation program associated with each second port, and wherein the control circuitry is further configured to provide the electrical stimulation program to the second port to which the connector is attached when the first address matches the second address of the second port to which the connector is attached.

9. The system of claim 1, wherein the cable comprises a wire for each at least one electrode, and at least one first wire.

10. The system of claim 9, wherein one of the at least one first wires is configured to provide the first address to the control circuitry.

11. The system of claim 10, wherein the one first wire is further configured to program the first address.

12. The system of claim 10, wherein another one of the at least one first wires is configured to provide power to the first circuit from the external trial stimulator.

13. A system, comprising:
a plurality of external assemblies, each comprising:
a first port configured to couple to a stimulation lead comprising at least one electrode for stimulating a patient's tissue,
a cable terminating at a connector, and
a first circuit comprising a first address of the external assembly; and
an external trial stimulator, comprising:
a plurality of second ports each having a second address and configured to receive the connectors, wherein the connectors are configured to be attachable and detachable from the second ports by a user, and
control circuitry configured to:
initially associate an external assembly with a corresponding one of the second ports by:
assigning the second address to the corresponding one of the second ports, and
programming the first address of the external assembly to match the second address of the corresponding one of the second ports,
read a first address of an external assembly and compare the first address to the second address of the second port to which the external assembly's connector is attached, and
perform an action when an external assembly's first address does not match the second address of the second port to which the external assembly's connector is attached.

14. The system of claim 13, wherein the action comprises generating an alert to the user.

15. The system of claim 14, wherein the alert is visual or audible.

16. The system of claim 13, wherein each first circuit comprises a fuse or antifuse each indicating one of the first addresses.

17. The system of claim 13, wherein each first circuit comprises a memory storing one of the first addresses.

18. The system of claim 13, wherein each external assembly comprises a box, wherein each box comprises one of the first ports and one of the first circuits.

19. The system of claim 18, wherein each cable extends from one of the boxes and terminates at one of the connectors.

20. The system of claim 13, wherein the external trial stimulator further comprises an electrical stimulation program associated with each second port, and wherein the control circuitry is further configured to provide each electrical stimulation program to its associated second port when each of the associated first and second addresses match.

21. The system of claim 20, wherein the action comprises providing the electrical stimulation program associated with a second port to a different second port on the external trial stimulator.

22. The system of claim 20, wherein there is a first stimulation program associated with a first of the second ports and a second stimulation program associated with a second of the second ports, wherein the action comprises providing the first stimulation program to the second of the second ports and providing the second stimulation program to the first of the second ports.

23. The system of claim 13, wherein each cable comprises a wire for each at least one electrode of its associated stimulation lead, and at least one first wire.

24. The system of claim 23, wherein one of the at least one first wires is configured to provide the first address to the control circuitry.

25. The system of claim 24, wherein the one first wire is further configured to program the first address.

26. The system of claim 24, wherein another one of the at least one first wires is configured to provide power to the first circuit from the external trial stimulator.

27. The system of claim 23, wherein one of the at least one first wires is configured to program the first address, provide the first address to the control circuitry, and provide power to the first circuit from the external trial stimulator.

28. A system, comprising:
an external assembly, comprising:
a first port configured to couple to a stimulation lead comprising at least one electrode for stimulating a patient's tissue, a cable terminating at a connector, and
a first circuit comprising a first address of the external assembly; and
an external trial stimulator, comprising:
a plurality of second ports each having a second address and configured to receive the connector, wherein the connector is configured to be attachable and detachable from the second ports by a user, and
control circuitry configured to:
initially associate the external assembly with one of the second ports by:
reading the first address in the external assembly, and
assigning the second address to the one of the second ports to match the first address,
read the first address and compare it to the second address of a second port to which the connector is attached, and
perform an action when the first address does not match the second address of the second port to which the connector is attached.

29. The system of claim 28, wherein the action comprises generating an alert to the user.

30. The system of claim 28, wherein the first circuit comprises a memory storing the first address.

31. The system of claim 28, wherein the cable comprises a wire for each at least one electrode, and at least one first wire.

32. A system, comprising:
a plurality of external assemblies, each comprising:
a first port configured to couple to a stimulation lead comprising at least one electrode for stimulating a patient's tissue,
a cable terminating at a connector, and
a first circuit comprising a first address of the external assembly; and
an external trial stimulator, comprising:
a plurality of second ports each having a second address and configured to receive the connectors, wherein the connectors are configured to be attachable and detachable from the second ports by a user, and
control circuitry configured to:
initially associate an external assembly with a corresponding one of the second ports by:
reading the first address in the external assembly, and
assigning the second address to the corresponding one of the second ports to match the first address,
read a first address of an external assembly and compare the first address to the second address of the second port to which the external assembly's connector is attached, and
perform an action when an external assembly's first address does not match the second address of the second port to which the external assembly's connector is attached.

33. The system of claim 32, wherein the action comprises generating an alert to the user.

34. The system of claim 32, wherein each first circuit comprises a memory storing one of the first addresses.

35. A system, comprising:
an external assembly, comprising:
a first port configured to couple to a stimulation lead comprising at least one electrode for stimulating a patient's tissue,
a cable terminating at a connector, and
a first circuit comprising a first address of the external assembly; and
an external trial stimulator, comprising:
a plurality of second ports each having a second address and configured to receive the connector, wherein the connector is configured to be attachable and detachable from the second ports by a user, and wherein the external trial stimulator comprises an electrical stimulation program associated with each second port, and
control circuitry configured to:
read the first address and compare it to the second address of a second port to which the connector is attached, wherein the control circuitry is configured to provide the electrical stimulation program to the second port to which the connector is attached when the first and second addresses match and to provide the electrical stimulation program to a port other than the second port to which the connector is attached when the first and second addresses do not match.

36. A system, comprising:
an external assembly, comprising:
a first port configured to couple to a stimulation lead comprising at least one electrode for stimulating a patient's tissue,
a cable terminating at a connector, wherein the cable comprises a wire for each at least one electrode, and at least one first wire, and
a first circuit comprising a first address of the external assembly; and
an external trial stimulator, comprising:
a plurality of second ports each having a second address and configured to receive the connector, wherein the connector is configured to be attachable and detachable from the second ports by a user, and
control circuitry configured to:
read the first address and compare it to the second address of a second port to which the connector is attached, and
perform an action when the first address does not match the second address of the second port to which the connector is attached,
wherein one of the at least one first wires is configured to program the first address, provide the first address to the control circuitry, and provide power to the first circuit from the external trial stimulator.

* * * * *